US009675252B2

(12) United States Patent
Mansoor et al.

(10) Patent No.: US 9,675,252 B2
(45) Date of Patent: Jun. 13, 2017

(54) SCANNING OPTICAL SYSTEMS (71) Applicants: BRITISH COLUMBIA CANCER AGENCY BRANCH, Vancouver (CA); THE UNIVERSITY OF BRITISH COLUMBIA, Vancouver (CA)

(72) Inventors: Hadi Mansoor, Burnaby (CA); Haishan Zeng, Vancouver (CA); Mu Chiao, Richmond (CA); Keqin Chen, Vancouver (CA)

(73) Assignees: British Columbia Cancer Agency Branch, Vancouver (CA); The University of British Colombia, Vancouver (CA)

( * ) Notice: Subject to any disclaimer, the term of this patent is extended or adjusted under 35 U.S.C. 154(b) by 528 days.

(21) Appl. No.: 14/347,304

(22) PCT Filed: Sep. 27, 2012

(86) PCT No.: PCT/CA2012/050678
§ 371 (c)(1),
(2) Date: Mar. 26, 2014

(87) PCT Pub. No.: WO2013/044388
PCT Pub. Date: Apr. 4, 2013

(65) Prior Publication Data
US 2014/0236022 A1    Aug. 21, 2014

Related U.S. Application Data (60) Provisional application No. 61/539,528, filed on Sep. 27, 2011.

(51) Int. Cl.
*A61B 5/00* (2006.01)
*A61B 1/00* (2006.01)
(Continued)

(52) U.S. Cl.
CPC ........ *A61B 5/0068* (2013.01); *A61B 1/00172* (2013.01); *A61B 1/0125* (2013.01); *G02B 21/241* (2013.01); *G02B 23/243* (2013.01)

(58) Field of Classification Search
CPC . A61B 1/00172; A61B 1/0125; A61B 5/0068; G02B 21/241; G02B 23/243
See application file for complete search history.

(56) References Cited

U.S. PATENT DOCUMENTS 4,840,457 A    6/1989   Remer
4,955,006 A *  9/1990   Fukushima ....... G11B 11/10515
                                                 360/59

(Continued)

FOREIGN PATENT DOCUMENTS

GB          2119538 A    11/1983

*Primary Examiner* — Bo J Peng
(74) *Attorney, Agent, or Firm* — Oyen Wiggs Green & Mutala LLP (57) ABSTRACT

Scanning mechanisms that have application in confocal imaging use electromagnetic actuation to move elements in an optical system. An objective lens mounted to a flexure comprising a magnetic material is actuated in the axial direction by an electromagnet coil. An optical path may pass through the coil. Scanning in transverse directions may be provided using magnetically actuated flexible beams which move the tip of an optical fiber or other pinhole in one or more transverse directions. Actuators may be actuated using driving currents that include an AC component and a DC bias component. The scanning mechanisms may be miniaturized and may be constructed to provide real-time imaging.

18 Claims, 8 Drawing Sheets

(51) Int. Cl.
*G02B 21/24* (2006.01)
*G02B 23/24* (2006.01)
*A61B 1/012* (2006.01)

(56) References Cited

U.S. PATENT DOCUMENTS

| | | | | |
|---|---|---|---|---|
| 5,107,107 | A * | 4/1992 | Osborne | G01D 5/34715 250/231.14 |
| 5,177,724 | A | 1/1993 | Gelbart | |
| 6,034,935 | A * | 3/2000 | Kim | G11B 7/0037 369/112.02 |
| 6,977,881 | B2 * | 12/2005 | Hashimoto | G11B 7/13927 369/112.02 |
| 7,102,992 | B1 | 9/2006 | Dalziel | |
| 2002/0139936 | A1 * | 10/2002 | Dumas | G01N 21/6452 250/458.1 |
| 2003/0063379 | A1 * | 4/2003 | Fukuyama | G02B 21/0032 359/390 |

* cited by examiner

SCANNING OPTICAL SYSTEMS

REFERENCE TO RELATED APPLICATIONS

This application claims priority from U.S. patent application No. 61/539,528 entitled MINIATURE CONFOCAL OPTICAL SYSTEM and filed on 27 Sep. 2011, which is hereby incorporated by reference for all purposes. For purposed of the United States of America, this application claims the benefit under 35 U.S.C. §119 of U.S. patent application No. 61/539,528 entitled MINIATURE CONFOCAL OPTICAL SYSTEM and filed on 27 Sep. 2011, which is hereby incorporated by reference herein for all purposes.

TECHNICAL FIELD

This invention relates to scanning optical systems. Some non-limiting example embodiments provide confocal imaging systems useful for imaging tissues in-vivo. Some embodiments provide confocal imaging heads that are deployable through an instrument channel of an endoscope.

BACKGROUND

Investigating whether a living subject is affected by certain conditions such as cancer, other pathological processes or diseases is often done initially by a physician who may observe the subject, possibly by eye or using observational tools such as endoscopes. If this visual observation identifies areas of tissue that appear to merit further investigation the physician may take a biopsy of the tissue. The biopsy may then be prepared for microscopic examination by a pathologist. A disadvantage of this procedure is that taking a biopsy is an invasive procedure. Also, transporting, tracking, preparing and examining the biopsy sample can be expensive and time consuming. There is a need for more efficient ways to perform diagnosis and/or screening for various conditions in vivo.

Various optical imaging techniques have been proposed. Such techniques may be applied in vivo to measure the thicknesses of tissue layers, study tissue structures, detect the presence of and/or spatial distribution of certain molecules or types of molecules in the tissues and the like.

In general, compared to non-optical methods, optical measurement techniques provide higher resolution and accuracy. Such techniques can approach the utility offered by histology images. However, conventional optical instrumentation cannot be readily used in endoscopic applications because the instrumentation is too large.

Various confocal imaging arrangements have been proposed for applications in vivo. In a confocal tissue imaging apparatus a spot of light is focused to a point in tissue. Backscattered light from the point in the tissue is collected and analyzed. The point at which the light is focused can be scanned through the tissue to provide a confocal image of the tissue. As with other optical imaging apparatus, it is a challenge to miniaturize confocal imaging apparatus to the point that it is small enough to use in certain applications. For example, it would be desirable to provide a miniature confocal imaging probe that is small enough to pass through the instrument channel of an endoscope that is typically a few millimeters in diameter. Another challenge is to avoid imaging artifacts arising from motions of the confocal imaging apparatus, Such motions arise mainly due to involuntary movements of the subject's body. Providing an imaging device capable of very rapid scanning of an area of tissue is one way to reduce the effect of such artifacts on image quality.

Two-dimensional tissue images may be provided in various planes. So-called 'vertical section' images are taken in planes extending into the tissue at least generally perpendicular to a surface of the tissue. Vertical section images are advantageous in part because pathology samples are typically prepared as vertical sections and pathologists and other medical professionals are trained to recognize features in vertical section images. Vertical section images also directly show the thickness of various tissue layers. Such layers are often arranged parallel to the tissue surface. Thickness measurements of biological tissues are useful for studying pathological processes and diseases. For instance, the thickening of epithelium in the vocal folds is an indicator of early laryngeal cancer. Another example is the measurement of the central corneal thickness that can be related to the intraocular pressure (TOP) to determine onset of glaucoma.

So-called horizontal sectional images are taken in planes extending generally parallel to the tissue surface. Three-dimensional images, are also useful for studying pathological processes and diseases.

SUMMARY

The invention has a number of different aspects. One aspect provides a scanning confocal imaging device. Some embodiments are small enough to pass through a channel that is a few mm in diameter (such as the instrument channel of an endoscope). Another aspect provides an optical head comprising a movable lens and/or a movable light source that may be used for confocal imaging but may be used in other applications as well. Another aspect provides an endoscope comprising a confocal imaging head. The confocal imaging head may be removable or non-removable from the endoscope. In some embodiments the confocal imaging head is removably disposed in an instrument channel of the endoscope. Another aspect provides confocal imaging devices operable to scan through a sample in one, two or three dimensions. In some example embodiments the imaging devices are operable to obtain vertical section images. In some example embodiments the imaging devices are operable to obtain horizontal section images. Other aspects provide methods for operating a scanning optical device.

Optical scanning mechanisms as described herein have applications that are not limited to confocal imaging. Such mechanisms may, for example, be applied to any imaging modality that operates by scanning a focused laser beam or other light beam. Some examples of such modalities are: reflectance confocal microscopy, fluorescence confocal microscopy, multi-photon microscopy, optical coherence tomography, CARS microscopy, coherent anti-stokes microscopy, Raman scattering microscopy, and the like.

Aspects of the invention provide a miniaturized confocal microscope device that incorporates MOEMS components. The system provides a 2-axis confocal scanner for vertical optical sectioning. The system can provide confocal measurements of the thickness of transparent films and biological tissues and can provide confocal images including images of in vivo tissues, biological specimens and clinical specimens.

In one aspect, the present invention provides a MEMS confocal system. The pinhole of this system is of fixed size and fixed position. Both the illumination beam and the collected tissue optical signals will pass through this pinhole, but in opposite directions. The collimating lens collimates the incident light coming from the pinhole and illuminates the entire focus/collection lens as well as a slightly larger area around it. The focus/collection lens focuses the beam to a micron size spot inside the sample under view. After having interacted with the sample, the elastically scattered laser light and the inelastically scattered Raman light are collected also by the focus/collection lens and relayed back to the pinhole by the collimating lens for confocal imaging and Raman spectroscopy. Thus the same pinhole serves as both the illumination pinhole and the detection pinhole to achieve confocality.

In another aspect, the present invention provides an apparatus for performing optical biopsies for diagnosis of cancer. The apparatus can be used for skin cancer diagnosis, cancers arising from the epithelium and additionally diagnosis of regions accessible by surgery.

In another aspect the present invention provides an apparatus for performing endoscopic views for diagnosis of cancer. Said endoscopic device is capable of visualizing otherwise inaccessible tissues such as lung bronchial epithelia, cervix or gastrointestinal tract. A still further aspect of the present invention provides an apparatus for measuring skeletal joints in combination with an arthroscopy system.

Another aspect of the invention provides real-time and non contact thickness measurement of biological tissue. In a further alternate aspect, the present invention provides real-time and non contact thickness measurement of transparent films. In a still further alternate aspect, the present invention provides real-time and non contact thickness measurement of semi-transparent or translucent films.

A further aspect of the invention permits measurement of tissue thickness for example for use in diagnosing or investigating disease such as laryngeal cancer and glaucoma.

Another aspect of the present invention provides an apparatus for scanning in X and Z dimensions. A beam of light is illuminated from a single mode optical fiber (SMF) and is collimated by a collimating lens. A collimating lens of fixed position and with a larger diameter than focus/collection lens is positioned so that the latter will receive constant total illumination intensity as it is scanned to different positions. The focus/collection lens can be scanned in both the lateral X-direction and the axial Z-direction. Fast-axis scanning may be performed by actuating the objective lens in an axial direction and slow-axis scanning may be done by moving the optical fiber in transverse direction or vise versa.

In some embodiments the focus/collection lens has a size of approximately 1 mm diameter or less while the collimating lens is the same size or slightly larger (e.g. 1.25 mm diameter or smaller). X-scanning and Z-scanning ranges of 100-200 μm or more may be provided. Example embodiments may provide scan rates of 1-30 frames per second and resolutions of 500×500 pixels.

Some embodiments include a control system that provides both full scanning and region of interest (ROI) scanning. During ROI scanning deflection of movable elements in one or more dimensions may be limited to ranges corresponding to a ROI.

Some embodiments may comprise a Raman spectroscopy subsystem. The Raman spectroscopy subsystem may comprises a light source such as an external cavity stabilized diode laser with a suitable wavelength (e.g. 785 nm or 830 nm), a transmissive imaging spectrograph (e.g. HoloSpec-f/2.2-NIR) with a suitable grating, an NIR-optimized back-illuminated, deep-depletion CCD detector (e.g. LN/CCD-EEV 1024, e256, QE, d75% at 900 nm), and a fiber-optic input port. Raman signals collected by the fiber optic are fed into the transmissive spectrograph, the holographic grating disperses the incoming light onto the liquid nitrogen-cooled CCD detector controlled by a computer. Raman spectra associated with NIR autofluorescence background may be displayed on the computer screen in real time and/or saved for further analysis.

In addition to the exemplary aspects and embodiments described above, further aspects and embodiments will become apparent by reference to the drawings and by study of the following detailed descriptions.

BRIEF DESCRIPTION OF THE DRAWINGS

Various non-limiting example embodiments are illustrated in the appended drawings.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
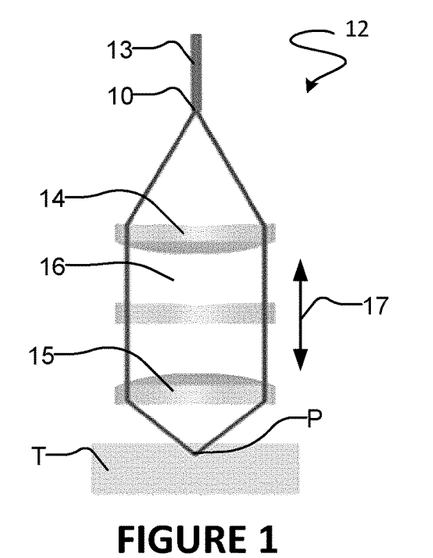
FIG. 1 is a schematic view of a confocal imaging device. The imaging device can be made to scan in one or more dimensions by one of or a combination of moving an objective lens axially and moving and end of the optical fiber in one or more dimensions.

FIG. 1 shows an example optical arrangement for confocal measurement. Light from a point-like light source 10 is delivered to illuminate a point P in tissue T by an optical system 12. In the illustrated embodiment, the end of an optical fiber 13 provides a point-like light source 10 and serves as a pinhole from which incident light (an illuminating beam) is emitted and through which received light (a reflected beam) is passed to a light detector (not shown in FIG. 1) after interacting with tissue T. Both the illuminating beam and the reflected beam pass through the pinhole but in opposite directions. In the illustrated embodiment, a laser beam is used as the illuminating beam.

In the illustrated embodiment, optical system 12 comprises a collimating lens 14 and an objective lens (or 'focusing lens') 15. Incident light passes through optical fiber 13. The tip of optical fiber 13 is at the focal point of collimating lens 14. Light issuing from the tip of optical fiber 13 is collimated by collimating lens 14 and is then focused onto point P by objective lens 15. In the illustrated embodiment the diameter of the collimated illuminating beam 16 is such that substantially the entire objective lens 15 is illuminated (i.e. the diameter of collimated beam 16 is substantially the same as the diameter of objective lens 15). Light originating from point P is collected by objective lens 15 and relayed back into optical fiber 13 for confocal imaging. The light originating from point P may include elastically-scattered light as well as light arising from fluorescence of material in tissue T at point P, inelastically-scattered light and the like. The collected light may be analyzed at a light detector connected to receive light from optical fiber 13.

One factor that can affect the performance of the confocal imaging arrangement is the numerical aperture of objective lens 15. Objective lens 15 has a relatively large numerical aperture in some embodiments. Selecting an appropriate numerical aperture for use in any particular application presents a trade-off. In general higher numerical apertures (for example 0.5 or greater) can provide better image resolution. However, usually lenses with high numerical aperture are characterized by larger clear apertures and shorter focal lengths. A larger clear aperture requires a larger collimated beam if the collimated beam is to cover the entire objective lens 15. Providing a larger-diameter collimated beam may require careful design of the optics of optical fiber 13 and collimating lens 14.

It is desirable that objective lens 15 have a focal length long enough to place the focal spot P at a desired depth in a sample through a window, if present. For typical applications, a confocal scanner will be housed in a suitable housing comprising a window through which light passes from and to objective lens 15. If the focal length of objective lens 15 is too short then it may be impossible to place focal spot P at a desired depth in the sample being imaged. A typical window has a thickness on the order of ½ mm. Also where objective lens 15 is movable in the axial direction some room must be left for objective lens 15 to move. Consequently, objective lens 15 should have a focal length of at least about 1 mm for typical applications. In some embodiments objective lens 15 is an aspheric lens to compensate for spherical aberration. Water or immersion oil may be used to improve the refractive index matching between the probe and the tissue being observed for better optical coupling in some applications.

Collimating lens 14 may also be an aspheric lens. It can be advantageous for collimating lens 14 to have a numerical aperture close to that of optical fiber 13 (for example 0.17). However, there is again a trade-off. A lens having a low numerical aperture may have a longer focal length. Increasing the focal length of collimating lens 14 results in demagnification in the system. When collimating lens 14 has a longer focal length the tip of optical fiber 13 needs to be moved farther to produce the same transverse displacement of focal spot P. Thus scanning the same area when using a collimating lens with a longer focal length can require a larger range of transverse movement of the tip of optical fiber 13 than would be required to scan the same area in a system using a collimating lens 14 having a shorter focal length.

A beneficial feature of the confocal imaging arrangement is that almost all light that is randomly scattered from tissue T (i.e. light arising from points in tissue T other than point P) will be excluded from optical fiber 13 and will not be collected. Hence confocal imaging can provide a signal-to-noise ratio (SNR) that is improved compared with other optical techniques.

An optical configuration, like that shown in FIG. 1 may be configured to allow point P to be scanned through tissue T. For example, point P may be scanned in the out-of-plane direction (generally perpendicular to the surface of tissue T) by moving objective lens 15 in the out-of plane direction as indicated by arrow 17. For example, objective lens 15 may be actuated to reciprocate back and forth in the out-of plane direction (which in the illustrated embodiment coincides with the optical axis of objective lens 15—i.e. axial scanning of objective lens 15).

Figure 2:
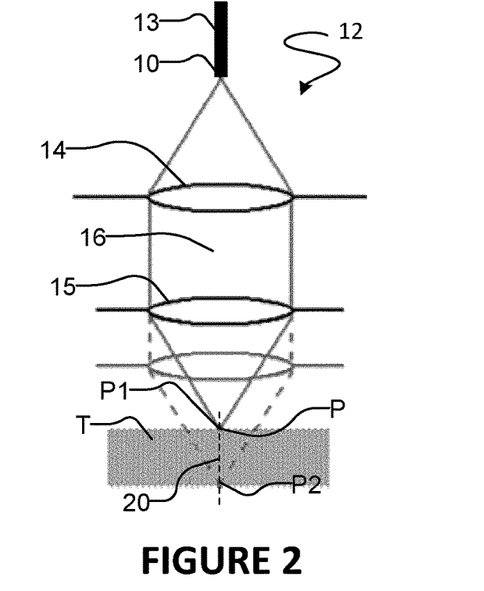
FIG. 2 is a schematic view of the confocal imaging device in FIG. 1 which illustrates the movement of an objective lens.

As illustrated in FIG. 2, scanning of point P in the out-of-plane direction while monitoring the intensity of detected light may be applied to measure the thickness of layers or other structures in tissue T. For example, objective lens 15 may be actuated so that the focal point P scans a line 20 perpendicular to tissue T. Changes in the intensity of the detected light will occur when point P is at a location where line 20 intersects a surface of tissue T or a boundary between portions of tissue T with different refractive indices. Typically the reflected light intensity is greater when focal point P is on the surface or at a boundary between tissue layers having different refractive indices (e.g. at points P1 and P2 shown in FIG. 2). Therefore, for a structure having such boundaries two intensity peaks will be detected each time the focal point scans across the thickness of the structure. The thickness of the structure can be determined by the distance between the locations of objective lens 15 at the time when the changes in intensity of the detected light are noted.

For example, objective lens 15 may be actuated such that its displacement d as a function of time is given or at least closely approximated by the sinusoidal equation of motion:

$$d = A \sin(\omega t) \qquad (1)$$

where A is the amplitude of actuation, ω is the frequency of actuation, and t is time. Knowing the amplitude and frequency of actuation, Eq. 1 may be used to convert detected light intensity as a function of time into a plot which represents the intensity signal as a function of displacement of objective lens 15. From the lens displacement between intensity peaks and the refractive index of the tissue being measured, the thickness of the layer or other structure in question can be calculated using the relationship:

$$t_s = \frac{n_s}{n_0} d \quad (2)$$

where: $t_s$ is the tissue thickness, $n_s$ and $n_0$ are the refractive indices of tissue and air respectively and d is the lens displacement between intensity peaks.

Figure 3:
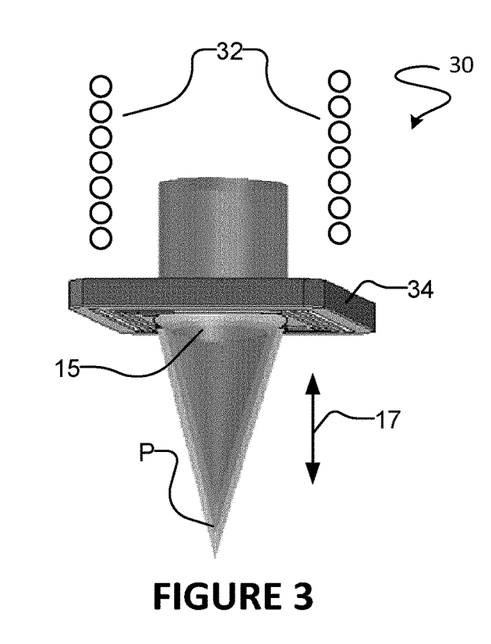
FIG. 3 is a schematic view of a beam of light passing through an objective lens mounted on a flexure.

One challenge is to provide a suitable mechanism for actuating lens, such as objective lens 15. In some embodiments electromagnetic force is used to actuate the objective lens. FIG. 3 is a conceptual illustration of an example actuator 30. In actuator 30, objective lens 15 is supported so that it can move in axial direction 17. An electromagnet 32 is located adjacent to objective lens 15. Electromagnet 32 may, for example, comprise a coil or solenoid. A power supply (not shown) may deliver a varying electrical current to electromagnet 32. The varying magnetic field of electromagnet 32 causes varying displacement of objective lens 15. Displacement of lens 15 may be caused by the interaction of the magnetic field of electromagnet 32 with a magnetic material that moves with objective lens 15. The magnetic material may, for example, comprise a ferromagnetic material that is on or in lens 15, a mount that holds lens 15 in place and/or a mechanism that supports lens 15.

In some embodiments, electromagnet 32 comprises a coiled conductor. Electromagnet 32 may have a hollow bore. A light path and optionally one or more optical elements may extend through the bore of electromagnet 32. In an example prototype embodiment electromagnet 32 was a coil made up of approximately 1000 turns of AWG #44 wire wound on a hollow cylindrical core. The coil had an outer diameter of 4 mm and was capable of producing a 14 mT magnetic field when driven with an AC current of 60 mA root-mean-square.

In an alternative embodiment, axial motion of lens 15 is actuated by interaction of a magnetic field with a current loop on the flexure. The current loop may comprise a current induced in the flexure or a conductor supported on the flexure by an alternating electromagnetic field or a current supplied from an external source. The magnetic field that interacts with the current loop may be provided by electromagnet 32 or by a permanent magnet. In such embodiments the lens support or central portion of the flexure may be made of a good electrical conductor such as copper to easily carry electrical current.

In some embodiments the magnetic field is augmented by a permanent magnet. In some embodiments, the magnetic field from electromagnet 32 causes motion of lens 15 by interacting with the magnetic field of a permanent magnet that moves with objective lens 15. The permanent magnet may, for example, be on or in lens 15, a mount that holds lens 15 in place and/or a mechanism that supports lens 15.

In the illustrated embodiment, lens 15 is supported on a resilient flexure 34 that allows lens 15 to move in an axial direction while biasing lens 15 back to a home position. The flexure resists movement of lens 15 in other directions.

In some embodiments, the flexure comprises a ferromagnetic material. Nickel is an example of a suitable material for flexure 34. In an alternative embodiment, a nickel alloy such as a silicon+nickel/iron alloy may be used, such an alloy may have similar magnetic properties to nickel and yet be mechanically stiffer. Other ferromagnetic materials such as iron or a suitable plastic containing particles of ferromagnetic material could be used. In some embodiments the flexure is formed in a sheet of nickel. Nickel is advantageous because there are well-developed processes suitable for fabricating nickel structures (e.g. laser cutting, MEMS fabrication processes). For example, a nickel foil may be cut into a suitable shape for use as flexure 34 by laser micromachining equipment. As another example, nickel may be electroplated in a shape suitable for use as flexure 34 on a silicon substrate. The substrate may then be etched away under the flexure until the flexure is supported only by a silicon frame. These and similar techniques may also be applied to other materials. In some embodiments, the flexure is fixed to a frame and lens 15 is mounted to the flexure. The frame may, for example, be made of silicon.

Flexure 34 may comprise a plurality of folded beams. In the example embodiment shown in FIG. 4, flexure 34 comprises four folded beams 42. Each folded beam 42 has a first end 42A attached to a frame 44 and a second end 42B attached to a central portion 45 on which a lens 15 may be mounted. Frame 44 central portion 45 and beams 42 that couple central portion 45 to frame 44 may all be integrally formed in a sheet of suitable material. Central portion 45 has an aperture 46 to pass light. Folded beams 42 can flex to allow center portion 45 to move in or out relative to frame 44 in a out-of-plane direction perpendicular to the plane of flexure 34. Flexure 34 is relatively rigid in directions other than the out-of-plane direction.

Figure 4:
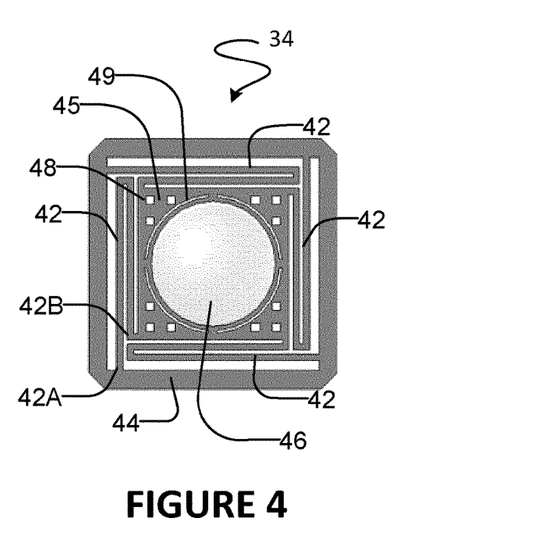
FIG. 4 is a plan view of an objective lens mounted on a flexure according to an example embodiment having four cantilever beams.

In the illustrated embodiment, additional holes 48 are provided in flexure 34. Holes 48 are provided to facilitate etching away of silicon under the flexure during fabrication. Also visible in the illustrated embodiment are narrow curved openings 49 which extend around aperture 46. Openings 49 assist in preventing adhesive that may be used to bond objective lens 15 to flexure 34 from flowing over flexure 34 during installation of objective lens 15. Openings 49 in flexure 34 can also advantageously permit air flow. This reduces viscous damping of the motion of flexure 34 thereby reducing energy loss and potentially providing greater displacements for the same energy input.

The dimensions of flexure 34 may be chosen to suit specific applications. For example, in some embodiments flexure 34 is made from nickel sheet having a thickness in the range of about 15 μm to about 150 μm. For example, working prototype embodiments have been made with the dimensions as set out in Table I.

TABLE I

Non-limiting example flexure dimensions

| Flexure material | Thickness | Width of folded beam | Total length of folded beam | Manufacturing process |
|---|---|---|---|---|
| nickel | 20 μm. | 75 μm | 4.8 mm | MEMS fabrication with electroplated nickel |
| nickel | 56 μm. | 125 μm | 8.7 mm | laser micromachining of nickel foil |

An objective lens may be mounted to a flexure of the type illustrated in FIG. 4 using a suitable adhesive such as a UV-curable adhesive.

When an external magnetic field is applied perpendicular to a nickel flexure 34, magnetic domains within the ferromagnetic nickel align with the applied field and the nickel becomes magnetized. As a result, the nickel flexure is attracted toward the source of the magnetic field. Folded cantilevers 42 permit the central part of the flexure 34 to move and therefore the lens starts to move in the out-of-plane direction when the flexure 34 is exposed to a magnetic field from electromagnet 32. When electromagnet 32 is driven by an electrical current that varies sinusoidally with time (with zero DC bias) the nickel flexure is actuated at a frequency that is twice the frequency of the applied electrical current. This double-frequency effect is expected since the flexure 34 is attracted toward electromagnet 32 regardless of the direction of the applied current.

In some embodiments flexure 34 is actuated at or near (e.g. within ±1% or e.g. within ±20 Hz) of its mechanical resonant frequency or a multiple of its mechanical resonant frequency while carrying lens 15. Driving motion of flexure 34 at or near its resonant frequency is advantageous because this provides a greater maximum amplitude of displacement of lens 15 at a lower power input than could be achieved while operating at other frequencies. Flexure 34 can be driven near its resonant frequency by driving electromagnet 32 with an AC current having a frequency of approximately ½ the resonant frequency (or a multiple thereof).

It is advantageous to drive flexure 34 with a driving force that has a frequency slightly different from the resonant frequency because under off-resonant conditions the motion of flexure 34 will be less sensitive to changes in environmental conditions than would be the case if flexure 34 were driven exactly at its resonant frequency. Environmental changes (e.g. changes in temperature) can alter the resonant frequency slightly. In some embodiments the driving frequency (which is twice the frequency of an AC signal driving electromagnet 32) differs from the resonant frequency of flexure 34 by at least 0.1%. The difference is at least 5 Hz in some embodiments. In other embodiments the difference is at least ¼% or at least ½% of the resonant frequency.

Flexure 34 may be driven, for example, by driving electromagnet 32 with an AC waveform having a frequency of approximately ½ of the resonant frequency of the flexure 34 carrying lens 15.

A larger objective lens 15 can provide better optical quality than a smaller lens. Improved optical quality can enhance the resolution of images; however, the increased mass of a larger lens reduces the resonant frequency of the lens actuator. This can reduce the imaging frame rate.

Assuming that the flexure 34 undergoes damped vibration under the magnetic driving force, the displacement of the flexure dz may be derived from a vibration equation of motion which yields:

$$d_z = \frac{F_{mag}}{k\left\{\left[1-\left(\frac{2\omega}{\omega_n}\right)^2\right]^2 + \left[2\zeta\frac{2\omega}{\omega_n}\right]^2\right\}^{1/2}} \quad (3)$$

where Fmag is the force applied by electromagnet 32, ω is the frequency of current in the electromagnet coil, $\omega_n$ is the natural frequency of the structure and k is the total stiffness of flexure 34 which is inversely proportional to the cube of the length of the folded beams. The flexure displacement as a function of current, I, in electromagnet 32 may be given as:

$$d_z = \frac{\mu_0 A N^2 l^3}{384 E I_g^2} i^2 \quad (4)$$

where $\mu_0$ is the permeability of free space, A is the cross-section area of the core of electromagnet 32, N is the number of turns in the coil of electromagnet 32, E is the Young's modulus of the material of flexure 32, I is the moment of inertia of the flexure, g is the size of the gap between electromagnet 32 and flexure 34 dz is the displacement of the flexure and l is the total length of each folded beam.

Figure 5:
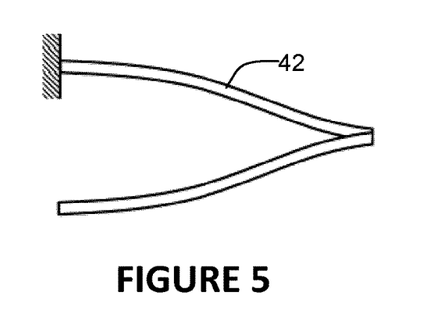
FIG. 5 is a plan view of a folded beam as may be used in a mechanism for scanning a lens in one dimension.

FIG. 5 illustrates the deformation of one folded beam 42 of an example flexure. The folded beam can be modeled as two fixed-guided beams connected in series.

Figure 6:
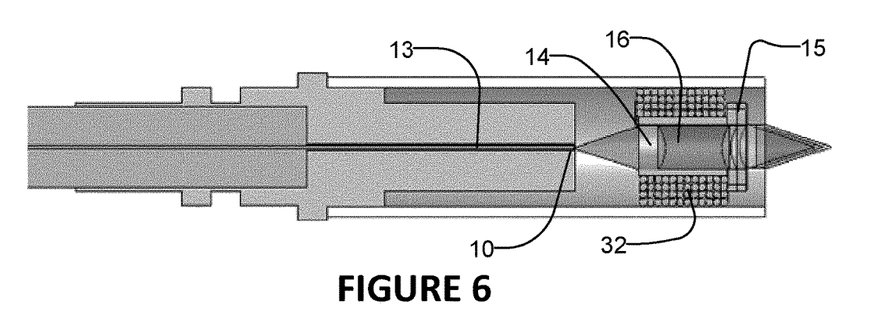
FIG. 6 is a cutaway view of a catheter according to an example embodiment containing a confocal imaging device.

As noted above, electromagnet 32 may be hollow or otherwise have an optical path extending through it. In some embodiments, one or more optical elements for example a collimating lens are placed inside the core of electromagnet 32. This structure, an example of which is illustrated in FIG. 6, can provide a very compact head for a confocal imaging system capable of scanning in the out-of-plane direction. Such a system may be used to provide a confocal scanning catheter. In an example embodiment the assembly illustrated in FIG. 6 has a rigid length of 30 mm or less and an outer diameter of 4.75 mm or less.

The theoretical axial resolution a confocal scanner as described above is approximated by:

$$\text{Resolution} = \sqrt{\left(\frac{0.88\lambda_e}{n-\sqrt{n^2-NA^2}}\right)^2 + \left(\frac{\sqrt{2}\,nPH}{NA}\right)^2} \quad (5)$$

where $\lambda_e$ is the laser wavelength, n is the refractive index of the medium and PH is the diameter of the pinhole. In an example confocal scanner objective lens 15 is a planoconvex lens having a numerical aperture (NA) of 0.43 and optical fiber 13 is a single-mode optical fiber with core diameter of 8.2 μm. Using Eq. 3 and assuming a laser wavelength of 785 nm, the theoretical axial resolution of the example scanner is 28 μm. Equation (5) demonstrates that the axial resolution of the scanner can be improved (made smaller) by using an objective lens 15 having a larger NA and an optical fiber having a smaller core diameter.

A scanner as described above which permits scanning of a focus point in the out-of-plane direction may be applied on its own (for example to measure the thicknesses of tissue layers) or may be applied in combination with mechanisms that permit scanning of the focus point in one or more other dimensions. For example a mechanism may be provided that moves the pinhole (e.g. the end of an optical fiber) transversely to the optical axis of objective lens 15 in combination with a mechanism that moves objective lens 15 axially to permit both axial and transverse scanning. Such a scanner may perform scanning of vertical sections in tissues being studied. The vertical sections may have resolutions sufficient to provide optical biopsies that mimic conventional histopathology examinations. The axially-movable part of the mechanism can be made to be very light in weight to facilitate fast scanning in the axial (Z) direction.

Tissues or other samples can absorb and scatter light. In some embodiments that perform scanning in the axial direction a control system is provided that modulates the intensity of incident light in time with scanning in the axial direction such that the incident light is more intense when the focus point is scanned to a location deeper in the sample and the incident light is less intense when the focus point is scanned to a location that is shallower in the sample. Such modulation can provide an image in which the exposure is more nearly equal across the image than would be the case if the incident light had a constant intensity. In some embodiments the brightness of a light source such as a laser is controlled to increases and decrease as the focus point is scanned into and out of the sample.

Figure 7:
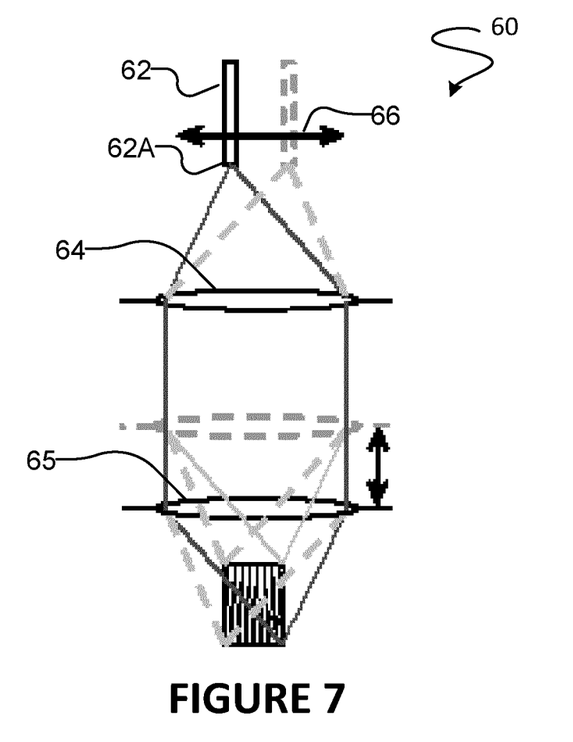
FIG. 7 is a schematic view of a confocal imaging device according to an example embodiment in which scanning in two dimensions may be performed. This view illustrates the movement of an objective lens and the movement of an optical fiber.

FIG. 7 shows optical components of an example 2-axis confocal scanner 60. In scanner 60, light from a light source (e.g. a laser—not shown in FIG. 7) is passed through an optical fiber 62 (which may be a single mode optical fiber). The light exits at the end 62A of optical fiber 62 and is collimated by a collimating lens 64. The collimated light travels to an objective lens 65 which focuses the collimated light to a focal spot within a sample (e.g. within tissue of a living subject).

Scanner 60 can scan a vertical section of the sample by performing both transverse and axial scanning of the focal spot. In some embodiments scanning of the focal spot in one dimension is significantly slower than scanning of the focal spot in the other dimension. For example, the focal spot may be slowly scanned in one dimension while it is being rapidly scanned back and forth in a perpendicular dimension to perform a raster scan over a two-dimensional area to be imaged. The frequency ratio and desired number of pixels in the image define the scanning rate of scanner 60. In some embodiments the scanning rate is faster than 1 Hz. Having a scanning rate of two or more complete scans per second, preferably 20 or more complete scans per second is advantageous.

In some embodiments, fast-axis scanning is performed by actuating objective lens 65 in the axial direction and slow-axis scanning is performed by moving the end of optical fiber 62 in a transverse direction 66 as shown in FIG. 7. In other embodiments the fast-axis and slow-axis are reversed so that fast-axis scanning is performed by actuating the end of optical fiber 62 to move transversely while slow-axis scanning is performed by moving the objective lens 65 in the axial direction.

Figure 8:
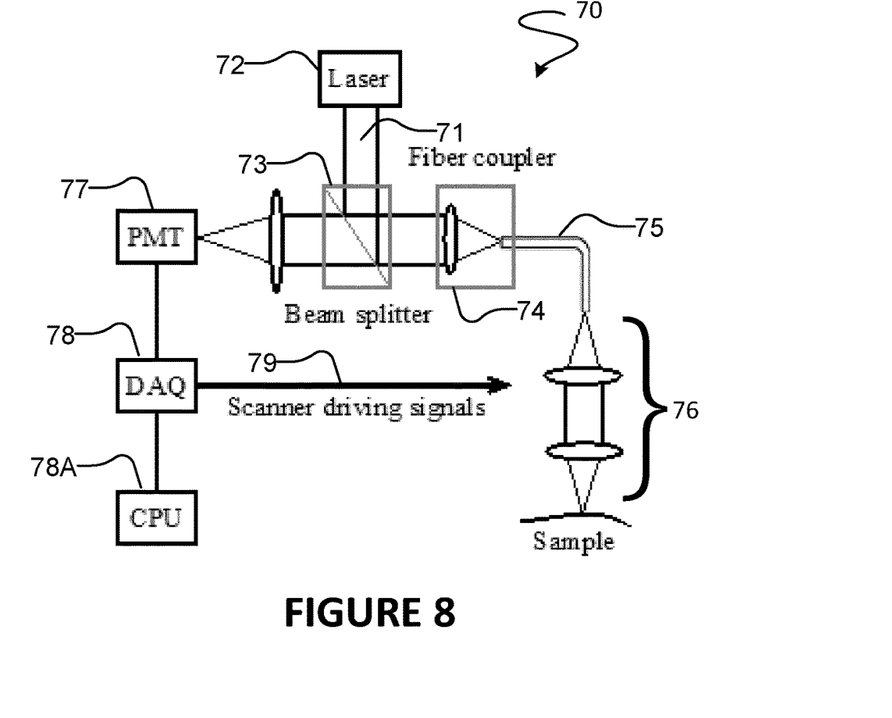
FIG. 8 is a schematic diagram of a confocal imaging device according to another example embodiment.

FIG. 8 is a schematic diagram of an example 2-axis confocal imaging system 70. A beam 71 of light is emitted from a laser source 72. The light of beam 71 is in the infrared. In an example embodiment the light has a wavelength of 785 nm. Beam 71 is directed by way of a beam splitter 73 to a single mode fiber coupler 74 which couples the light into an optical fiber 75. Beam splitter 73 may, for example, be a 30R/70T beam splitter (meaning that 30% of incident light is reflected while 70% of incident light is transmitted). Using a beamsplitter that transmits a high proportion of light from the sample to the light detector is advantageous as it can result in greater signal to noise ratio at the cost of requiring a more intense light source to deliver the same amount of light to the sample. In some embodiments Laser beam 71 is polarized, optical fiber 75 is of a type that maintains polarization of transmitted light and beamsplitter 73 is a polarizing beam splitter. The use of polarized light with a polarizing beamsplitter can help to reject ambient light as well as light reflected from surfaces of optical components in the system (e.g. the surface of optical fiber 75) to enhance imaging contrast.

Optical fiber 75 carries the light to a scanning head 76 that can scan a focal spot in one, two or three dimensions. Light reflected from the focal spot in the sample is relayed by way of optical fiber 75 and beam splitter 73 to a light detector 77 (e.g. a photomultiplier tube (PMT), a spectrometer, an avalanche photodiode (APD) or the like). A data acquisition (DAQ) system 78 is used to collect the intensity signal from the PMT and to generate driving signals 79 for the scanning head 76. The intensity signal is converted to a two-dimensional image using a computer 78A.

In some embodiments, transverse motion of a pinhole (e.g. the end of an optical fiber) is electromagnetically driven. An electromagnetic transverse actuator may comprise a small electromagnet located where it can apply a time varying transversely-oriented magnetic force to pull a resiliently-mounted end of the optical fiber toward the coil. In an example embodiment an end portion of the optical fiber is attached to a resiliently flexible member that is made of a ferromagnetic material or has a piece of ferromagnetic material attached to it. The resiliently flexible member may comprise a beam. The resiliently flexible member may, for example, comprise a nickel beam or tube.

To prevent the end of optical fiber 62 from scanning in unwanted directions due to misalignment with the applied magnetic field or external vibrations, the member that supports optical fiber 62 may be made to be much less stiff with respect to bending in one direction than it is with respect to bending in other directions. For example, stiffness for bending about an X-axis can be designed to be much smaller than that for bending about a Y-axis perpendicular to the X-axis.

This can be achieved, for example, by mounting optical fiber 62 on a cantilever beam. The cantilever beam may be significantly thinner in one transverse direction than it is in another transverse direction. Since the force required to deflect a beam varies as $t^3$ it is easy to make a beam that is 500 or more times less stiff with respect to bending in one transverse direction than it is with respect to bending in a second transverse direction perpendicular to the first transverse direction. For example, in some embodiments, the cantilever beam is 25 mm long×2 mm wide by 25.4 μm thick. In some embodiments the cantilever beam has a ratio of width to thickness of at least 10:1.

A longitudinal groove may be provided along the length of the cantilever beam to hold optical fiber 62. One end of the cantilever beam may be fixed (for example, mounted to a v-groove fiber holder). An electromagnetic coil may be placed near the other (free) end of the cantilever beam. The cantilever beam may comprise or support a ferromagnetic material so that when an alternating magnetic field is generated by the coil, the cantilever beam is repeatedly pulled toward the coil and released resulting in forced transverse actuation of the optical fiber. In some embodiments, the length of the cantilever beam is 25 mm and the tip of the fiber projects 5 mm past the end of the cantilever beam. In a prototype embodiment with this construction the tip of the optical fiber could be moved transversely by 450 μm in the X direction.

Figure 9:
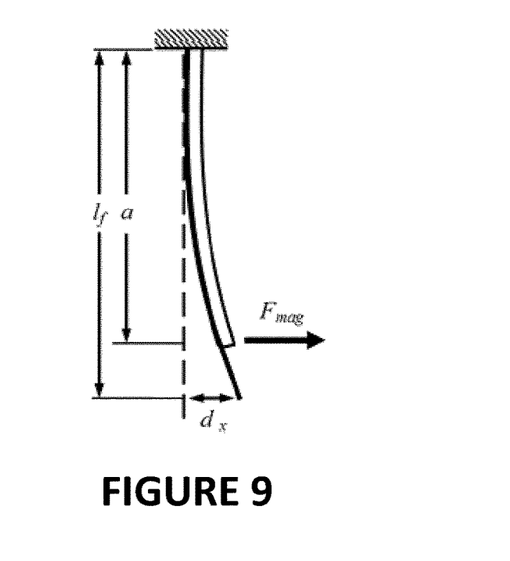
FIG. 9 is a plan view of a cantilever beam as may be used in a mechanism for scanning a light source in one dimension.

The cantilever beam undergoes simple forced actuation and can be modeled as a beam with one end fixed and the other end free (see FIG. 9). The deflection, $d_X$, at the tip of the fiber can be approximated by:

$$d_x = \frac{F_{mag} a^2}{6EI}(a - 3l_f) \quad (6)$$

where $F_{mag}$ is the electromagnetic force exerted on the beam, $l_f$ is the length of the end portion of the fiber, a is the length of the beam, I is the moment of inertia and E is Young's modulus of the beam.

Figure 10A:
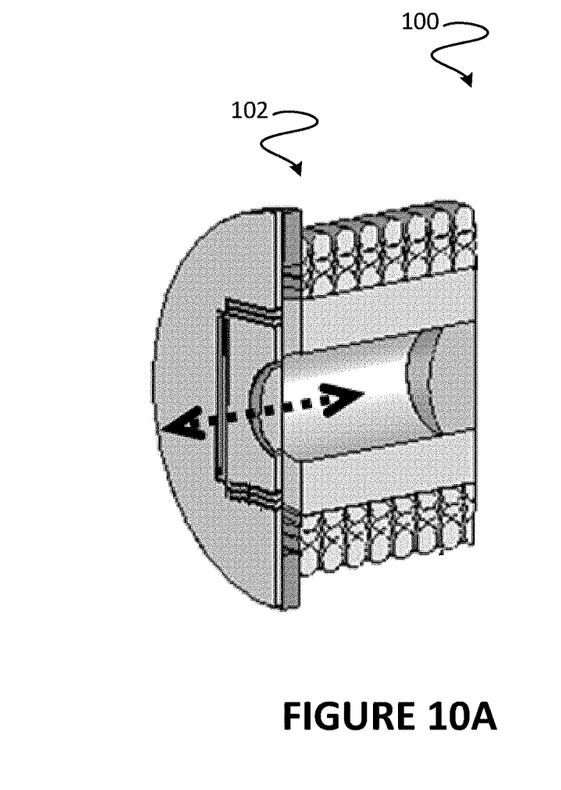
FIGS. 10A and 10B are an isometric views of different portions of a confocal imaging device according to another example embodiment.
Figure 10B:
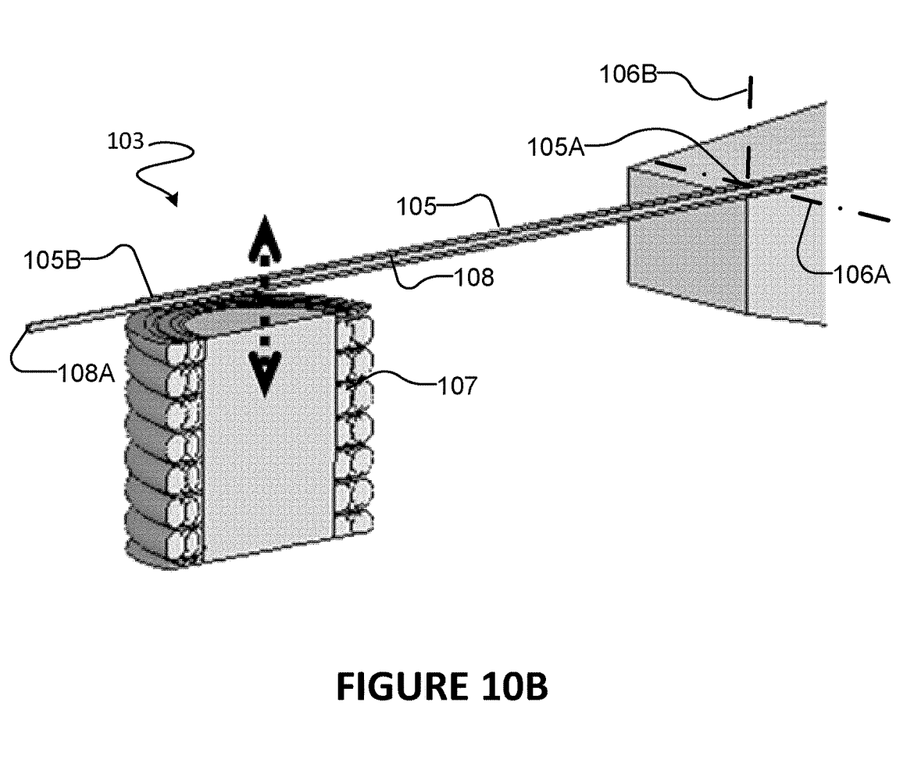

FIGS. 10A and 10B are cross-section views showing different portions of an example 2-axis scanner 100. Scanner 100 includes an actuator assembly 102 for axial scanning (FIG. 10A) and an actuator assembly 103 for transverse scanning (FIG. 10B). Axial actuator assembly 102 may, for example, have a structure as shown in FIGS. 3, 4, and 6, and as described above. Transverse scanning assembly 103 comprises a cantilever beam 105 having a fixed end 105A and a free end 105B. Cantilever beam 105 is most flexible about a bending axis 106A and is much stiffer with respect of an axis 106B that is perpendicular to axis 106A.

An electromagnet 107 is located adjacent to but spaced apart from free end 105B of cantilever beam 105. Electromagnet 107 is on a side of cantilever beam 105 toward which cantilever beam 105 moves when bent about more flexible bending axis 105A. Optical fiber 108 is mounted to cantilever beam 105 so that its tip 108A moves transversely when cantilever beam 105 is caused to vibrate toward and away from electromagnet 107.

In some embodiments, cantilever beam 105 is made of nickel or another ferromagnetic material. In an example system, lens and fiber actuators (102, 103) exhibit sinusoidal responses when the corresponding electromagnets are driven with sinusoidal current waveforms with peak-to-peak displacement amplitudes of 190 µm and 450 µm respectively.

In an example system, lens actuator 102 is actuated at its resonant frequency of 378 Hz and the cantilever beam is actuated at 2 Hz. In this example system the imaging frame rate is 2 frames per second when imaging is performed only when the cantilever beam is moving in one direction. The imaging frame rate could be doubled by imaging in both directions of motion of the cantilever beam. In other embodiments, the cantilever beam structure of actuator 103 is actuated at or near to its resonant frequency (or a multiple thereof such as twice the resonant frequency). In some embodiments the resonant frequency of the cantilever beam/optical fiber in actuator 103 is higher than that of the flexure/lens of actuator 102 and actuator 103 is driven to operate as the fast axis for raster scanning while actuator 102 is driven to operate as the slow axis for raster scanning. In such embodiments a larger, higher in optical quality objective lens may be carried by actuator 102 while maintaining a high frame rate.

Figure 11:
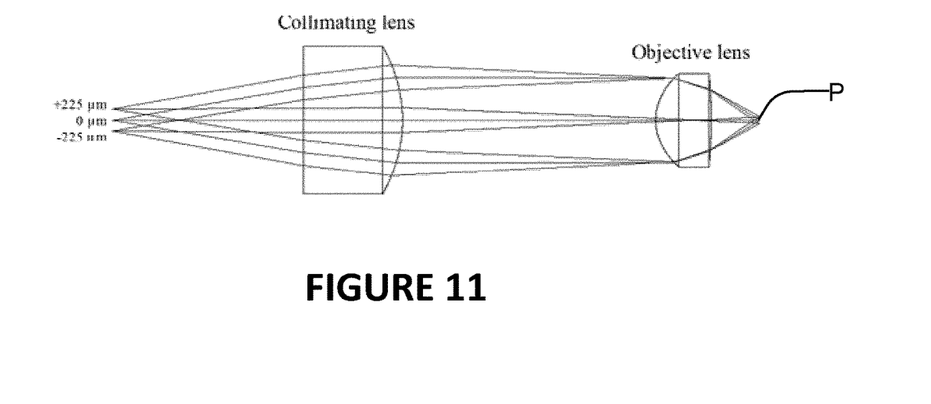
FIG. 11 is a schematic view of an example arrangement of lenses in a confocal imaging device. The paths of different beams of light through the lenses are illustrated.

FIG. 11 shows the path of representative beams of light through the collimating lens and objective lens of actuator 103 while the optical fiber is actuated to move transversely by ±225 µm. It can be seen that the transverse movement of the end of the optical fiber results in a corresponding transverse movement of the focal spot P in the sample being scanned.

The field of view of an example prototype scanner constructed as described herein is 145 µm in a transverse direction and 190 µm in an axial direction. The lateral and axial resolutions of the prototype scanner are 3.87 µm and 10.68 µm respectively.

Figure 12:
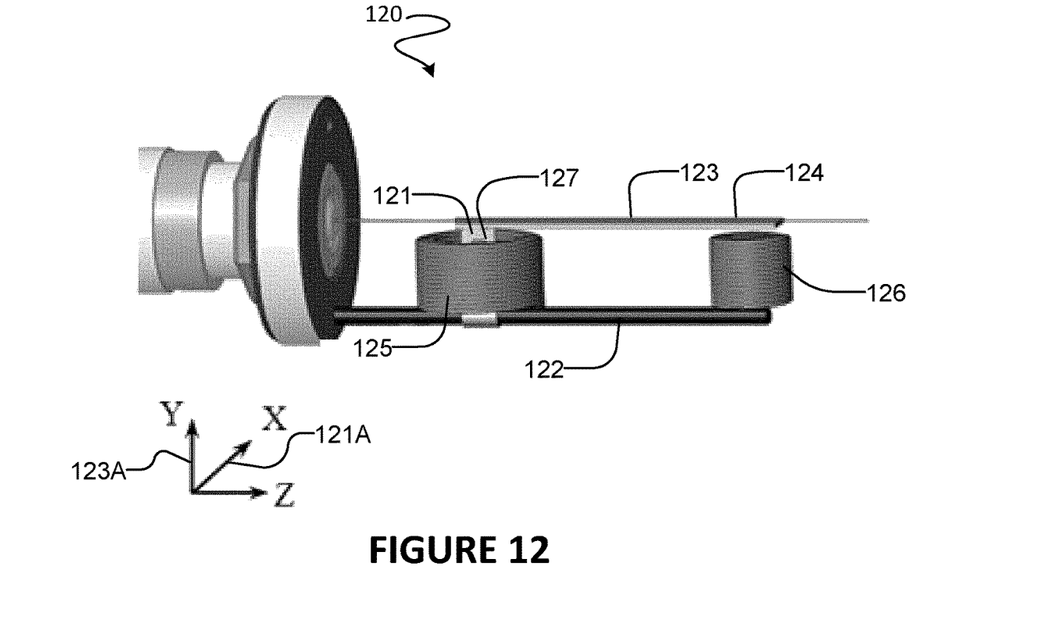
FIG. 12 is a schematic view of a confocal imaging device according to another example embodiment which can scan in two dimensions.

An electromagnetically operated actuator may also be configured to scan in two transverse directions which may be perpendicular to one another. FIG. 12 shows the construction of an example two dimensional actuator 120 (which can be used with fixed optics, for example, to provide imaging of horizontal sections, or, optionally, with optics that provide scanning in an axial (or 'Z') direction, for example to provide three-dimensional scanning and/or scanning in any selected pair of dimensions and/or scanning in one dimension (e.g. for tissue layer thickness measurements).

Scanner 120 comprises two cantilever beams (121 and 123) that have bending axes at right angles to one another. Beam 121 is attached to a support (e.g. rod 122) and is compliant in bending in the X direction as shown by arrow 121A. Beam 123 is attached to a free end of beam 121 and is flexible in the Y direction as indicated by arrow 123A.

Optical fiber 124 is attached to beam 123. The tip of optical fiber 124 can be moved in the X direction by causing beam 121 to bend. The tip of optical fiber 124 can be moved in the Y direction by causing beam 123 to bend.

Bending of beams 121 and 123 can be actuated electromagnetically. In the illustrated embodiment an electromagnetic coil 125 actuates bending of beam 121 and an electromagnetic coil 126 actuates bending of beam 123.

One or more permanent magnets 127 are attached to beam 121 at a location spaced apart from support 122. Magnet(s) 127 are arranges such that magnetic poles project to either side of beam 121 with N poles on one side of beam 121 and S poles on the other side of beam 121. The poles have one magnetic polarity (N or S) on one side of beam 121 and the opposite magnetic polarity (S or N) on the opposite side of beam 121. Various arrangements of magnets 127 are possible. For example, magnet 127 could comprise a single bar magnet extending through an aperture in beam 121 with its poles projecting to either side of beam 121. As another example, magnet 127 could comprise two permanent magnets, one mounted on each side of beam 121 with their poles oriented such that opposite poles of the two magnets are projecting away from beam 121.

Figure 13:
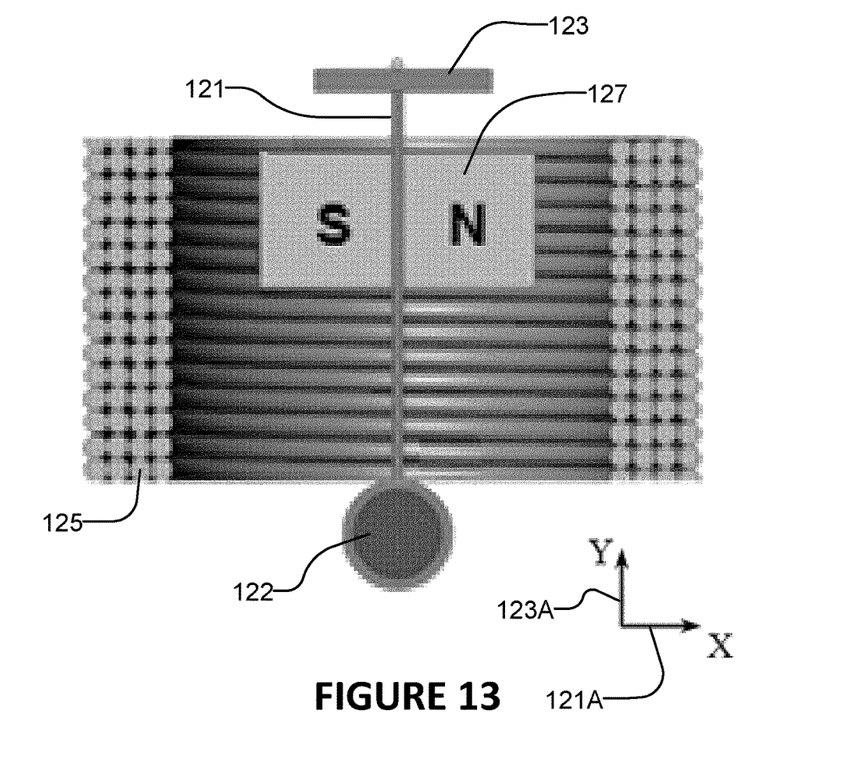
FIG. 13 is a cutaway view of a portion of the confocal imaging device illustrated in FIG. 12.

Coil 125 has a hollow-core and is placed around beam 121 in the vicinity of magnets 127 (see FIG. 13). When electric current passes through the conductors of coil 125, the resulting magnetic field causes a force on the N poles directed generally parallel to a centerline of coil 125 and a force on the S poles in the opposite direction. The result is a bending moment applied to beam 121 that causes the free end of beam 121 to move in the X direction carrying beam 123 along with it.

In some embodiments, the permanent magnets are made of rare earth metals such as neodymium. In some embodiments two permanent magnets are used and they are attached to either side of beam 121.

Coil 126 is positioned adjacent to and spaced apart from the free end of beam 123. Beam 123 comprises a ferromagnetic material so that it is attracted toward coil 126 when electrical current is passing through coil 126. This causes beam 123 to bend and moves the tip of optical fiber 124 in the Y direction. In some embodiments, coils 125 and 126 are attached to the same support.

In a non-limiting example embodiment, beam 121 is 2.4 mm wide, 12 mm long and 0.11 mm thick and beam 123 is 2 mm wide, 4.5 mm long and 0.05 mm thick. The longitudinal axes of beams 121 and 123 may be oriented at right angles to one another. The major surfaces of beams 121 and 123 may also be oriented at right angles to one another.

One scanning mode can be achieved by applying an alternating or pulsating electrical current to coil 126 to generate a magnetic field that causes beam 123 to vibrate in the Y direction. A second scanning mode can be achieved by applying an alternating or pulsating electrical current to coil 125 thereby causing the tip of optical fiber 124 and beam 123 to vibrate. Beams 121 and 123 can be actuated at different frequencies to cause the tip of optical fiber 124 to move in a raster scanning pattern. Coils 125 and/or 126 may be actuated with constant currents or high frequency currents to cause beams 121 and/or 123 to hold desired positions.

In some embodiments beams 121 and 123 are constructed to have much higher bending and twisting stiffness in all directions other than for bending about the intended bending axis (e.g bending about axes parallel to the Z-axis to yield displacement in the X direction for beam 121 and bending about axes parallel to the X-axis to yield displacement in the Y direction for beam 123).

Figure 14:
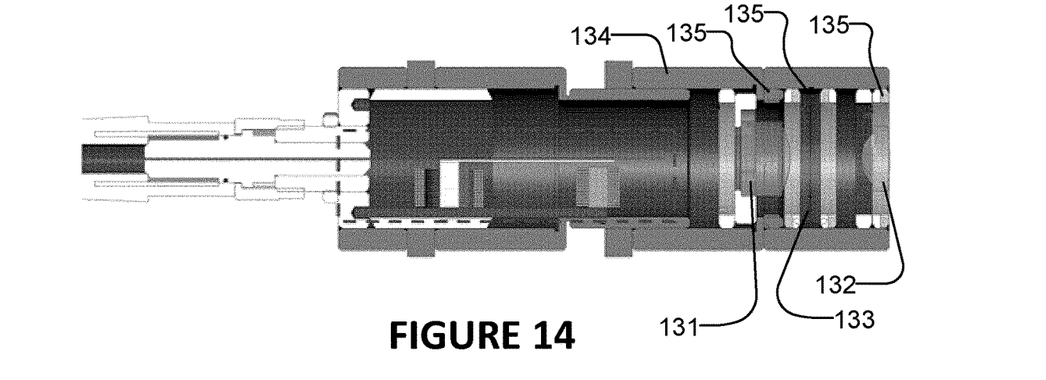
FIG. 14 is a cutaway view of a catheter according to another example embodiment containing a confocal imaging device which can scan in two directions.

In some embodiments, the 2-axis fiber actuator along with any associated lenses and wave plates may be assembled in a protective tube (for example a standard ½ inch tube). A schematic diagram of an imaging system incorporating an actuator as described herein is shown in FIG. 14. Lenses 131 and 132 and a wave plate 133 are positioned and secured in place in a tube 134 by retaining rings 135. An adjustable lens tube is used to align the optical fiber at the focal point of the collimating lens. An example adjustable lens tube is the model SM05 lens tube available from Thorlabs Inc. of Newton N.J. USA. Locking rings may be used in conjunction with an adjustable lens tube to fix the collimating lens in place and to hold the collimating lens at the desired distance from the tip of the optical fiber.

Fast actuation of a laser spot can be achieved by actuating beam 123 at or near its resonant frequency. This may be done by applying a sinusoidal current to coil 126 at half the resonant frequency of beam 123 (with no DC bias). The resulting magnetic force varies at twice the frequency of the current applied to the coil. The magnetic force is always directed toward the coil, regardless of the direction of the current.

In some embodiments, raster scanning of the laser beam may be achieved by actuating beam 123 to vibrate in the Y direction at or near its resonant frequency (fast axis) and actuating beam 121 to move back and forth in the X direction at a lower frequency of e.g. 2 Hz to 3 Hz. In some embodiments, beam 123 has a resonant frequency of at least 500 Hz, preferably higher (such as at least 600 Hz, or at least 800 Hz or at least 1000 Hz). As described above with reference to actuator 30 it can be advantageous to drive vibration of cantilever beam 123 with a driving force having a frequency that differs slightly from the resonant frequency of cantilever beam 123 (carrying optical fiber 124). The difference can be small, for example in some embodiments the driving frequency (which, for the case of an AC waveform driving coil 126 is twice the frequency of the AC waveform) differs from the resonant frequency of cantilever 123 by at least 0.1%. The difference is at least 5 Hz in some embodiments. In other embodiments the difference is at least ¼% or at least ½% of the resonant frequency of cantilever 123 (or a multiple thereof).

In some embodiments, the scanning speed of the device is 6 frames per second with optical resolutions of 8.45 µm and 1.17 µm in axial and transverse directions.

Advantageously, a scanner 120 can be made so that scanning in two transverse dimensions (e.g. an X direction and a Y direction) can be done independently. To facilitate the independence of the motions in the two transverse dimensions, beam 121 may be made to be significantly stiffer than beam 123. Beam 121 functions as a base for mounting beam 123.

Some advantages of using electromagnetic forces to actuate scanning as described herein (it is not necessary that all embodiments have any of these advantages) include: electromagnetic actuators as described above can be designed to provide relatively large scanning ranges; electromagnetic actuators as described above can be designed to operate using low driving voltages as is desired or required in certain clinical applications; the optical configuration and the mechanical design of the scanning head provides easy optical alignment and replacement of components; a confocal scanner design can include out-of-plane lens actuator for vertical section imaging and/or for three-dimensional imaging.

Devices as described herein may be used to facilitate non-invasive clinical diagnosis and evaluation of diseases such as skin and oral cancers. The device may also be miniaturized to provide a catheter for endoscopic applications. For example, a probe having a diameter of 3 mm or 3.2 mm will fit into the instrument channels of typical colonoscopes. A probe having a diameter of 1.6 mm or 1.8 mm will fit into the instrument channels of typical bronchoscopes. Some embodiments of the invention provide an endoscope such as a bronchoscope or a colonoscope supplied together with a probe sized to be received within an instrument channel of the endoscope wherein the probe comprises an optical scanning system as described herein. A physician or other user may use the endoscope to locate tissues of interest and then operate an imaging system including the probe to obtain images (which may include vertical section images) of the tissues of interest. The user may view the images in real time. Since the images are electronic, the user may transmit those images for review by a pathologist, if desired. Based on the images, the user may decide to obtain a biopsy of the imaged tissue. In some embodiments an imaging probe as described herein is integrated into the shaft of a biopsy forceps such that the user can operate the forceps to acquire a biopsy sample without removing the imaging probe from the endoscope.

Use of scanning optics as described herein is not limited to imaging applications. For example, such scanning optics may be applied to focus a laser beam at a selected point or points within tissues for therapeutic purposes.

Images obtained by scanning a light beam or focus point using one or more actuators may be distorted due to non-linear dynamics of the actuators, particularly when the position of the actuators is assumed and not measured. For example, during system characterizations of an example device, the inventors noted that the peak amplitudes of vibration of beam 123 as measured by a Laser Doppler Vibrometer (LDV) were not equal. This resulted in a wavy pattern in reconstructed images. In the confocal images, every other line was shifted down by a few pixels, resulting in an unwanted pattern in the image. This distortion may be corrected by post-processing of image data using tools such as ImageJ™ or MATLAB™; however, for clinical applications it is advantageous to obtain artifact-free images in real-time.

It was found that the wavy pattern could be reduced or eliminated by driving coil 126 with a sinusoidal current with a frequency equal to the resonant frequency of beam 123 with an added DC bias current.

Figure 15:
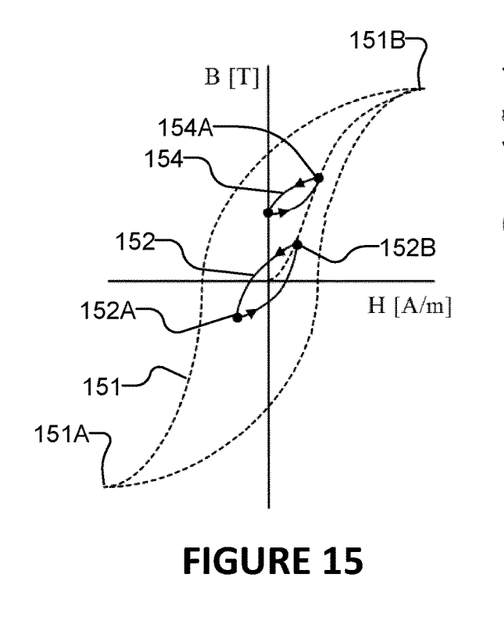
FIG. 15 is a graph showing example magnetization curves for a magnetic material.
Figure 16:
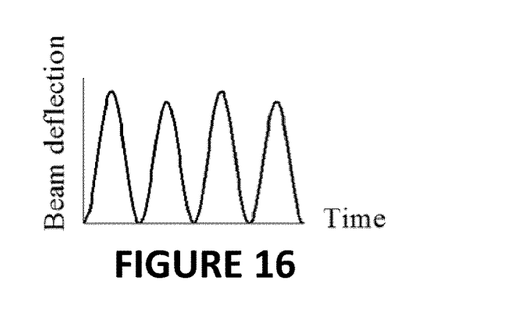
FIG. 16 is a graph showing the deflection of a beam over time.

It is believed that the operation of the correction method described herein can be understood by considering a typical magnetization curve (B-H curve) for a magnetic material (FIG. 15). The loop 151 indicated by the dashed line is the major hysteresis loop. Tips 151A and 151B represent magnetic saturation. Assuming a magnetic field is cycling at low amplitudes, when a sinusoidal current with half the resonant frequency of beam 123 and no DC bias is applied to coil 126, the magnetism induced in beam 123 will travel around minor loop 152. Points 152A and 152B on loop 152 correspond to the forces applied to the beam at its actuation peaks (see FIG. 16). Any asymmetry in loop 152 with respect to the horizontal axis will result in inequality of the magnetic forces on beam 123 during the corresponding half-cycle of the driving current and corresponding inequality in the actuation amplitudes of beam 123. Asymmetry in loop 152 can arise, for example, from initial small biases in the driving signal. Temperature effects and magnetic memory of the core of coil 126 and beam 123 may also contribute to the shift.

Figure 17:
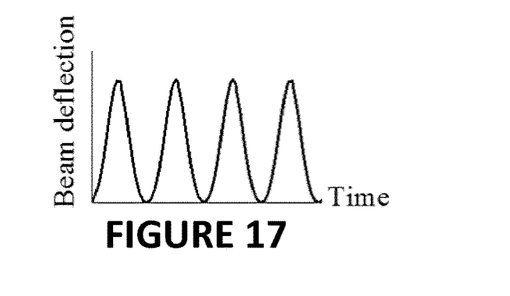
FIG. 17 is a graph showing the deflection of a beam over time.

By adding a DC bias to the current used to drive coil 126, the minor loop can be shifted to the positive region of the B-H curve as shown by loop 154. In this case the magnetic field remains unidirectional and magnetic force is independent of the initial state of magnetic field. When current frequency is doubled, point 154A on loop 154 corresponds to equal magnetic forces applied to beam 123 at all deflection peaks (see FIG. 17). These forces result in equal actuation amplitudes and a confocal image with reduced distortion. This technique (driving an actuating electromagnet with a signal that includes a DC bias and has a doubled frequency so that the driving signal is always positive) may also be used to drive an actuator for axial scanning of a lens as described above.

Figure 18:
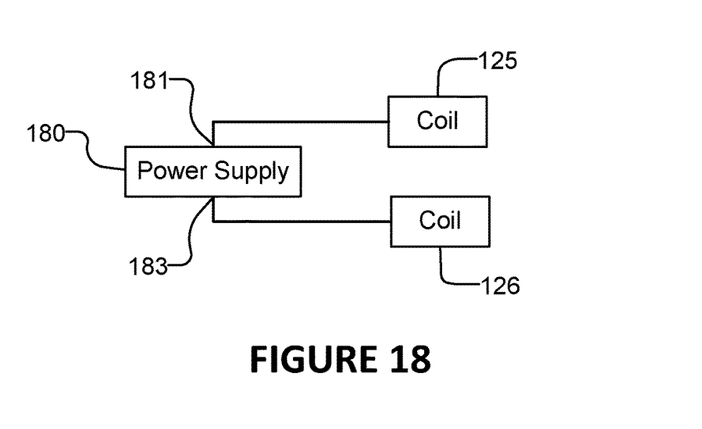
FIG. 18 is a schematic diagram showing an electromagnetic driving system for a scanning imaging device.

FIG. 18 illustrates an example driving system for a two-axis scanner. A power supply 180 has outputs 181 and 183 respectively connected to supply current to coils 125 and 126. Power supply 180 is configured to provide suitable driving currents to each of coils 125 and 126. For raster scanning the current delivered to one of coils 125 and 126 that is selected as a fast scanning axis (typically coil 126) alternates or fluctuates at a relatively high frequency (preferably approximately ½ the resonant frequency of the driven structure or a multiple thereof) while the current delivered to the other one of coils 125 and 126 (typically coil 125) alternates or fluctuates at a significantly lower frequency. In some embodiments the frequency of the waveform delivered to the fast axis coil is selected to be at or near a resonant frequency of the structure being driven (i.e., in the case of coil 126, a resonant frequency of beam 123 carrying optical fiber 124) or a multiple thereof. The waveforms of the currents supplied by power supply 180 may be sinusoidal, triangular or have other shapes. Sinusoidal waveforms are generally convenient and provide good results.

Power supply 180 may be configured to supply a DC bias to one or both of the current signals. The DC bias may be adjustable. User controls may be provided to allow users to set the amplitudes of the current waveforms (thereby adjusting the dimensions of a scanned area or volume) and the DC biases (thereby allowing adjustment of image quality).

Various methods may be used to manufacture the apparatuses described herein. For example the flexure and cantilever beams may be manufactured by electroplating, chemical etching, laser machining, or other methods.

Devices as described herein may be packaged in a protective housing. For example, such devices may be contained within a small tube made of a non-magnetic material. A window in the housing is placed close to the objective lens. The window is advantageously thin while being strong enough to withstand being pushed against tissue for imaging. A thin window placed close to the objective lens facilitates an increased depth of scan into the tissue of a subject. The housing is preferably of a material that can be sterilized using commonly-available sterilization procedures.

Certain embodiments, including embodiments illustrated in the accompanying drawings have the advantage of a direct straight optical path between a pinhole (e.g. the tip of an optical fiber) and the focus point. Mirrors are not required in this part of the scanning mechanism.

Methods and apparatus as described herein may be used in imaging a wide range of samples including tissues in vivo. In some embodiments the methods and apparatus are applied to image tissues such as skin, ling tissues, cervical tissues, tissues of the gastro-intestinal tract, and so on.

Interpretation of Terms

Unless the context clearly requires otherwise, throughout the description and the claims:

- "comprise," "comprising," and the like are to be construed in an inclusive sense, as opposed to an exclusive or exhaustive sense; that is to say, in the sense of "including, but not limited to".
- "connected," "coupled," or any variant thereof, means any connection or coupling, either direct or indirect, between two or more elements; the coupling or connection between the elements can be physical, logical, or a combination thereof.
- "herein," "above," "below," and words of similar import, when used to describe this specification shall refer to this specification as a whole and not to any particular portions of this specification.
- "or," in reference to a list of two or more items, covers all of the following interpretations of the word: any of the items in the list, all of the items in the list, and any combination of the items in the list.
- the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a lens, electromagnet, cantilever beam, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:

1. An optical scanning device comprising:
   a flexure comprising a ferromagnetic material, the flexure having a mounting portion movable in an axial direction;
   a first lens mounted to the mounting portion of the flexure; and
   an electromagnet adjacent to the flexure and spaced apart from the flexure in the axial direction;
   wherein:
   an optical path of the scanning device extends through a core of the electromagnet;
   the optical scanning device comprises: one or more optical elements located within the core of the electromagnet, the one or more optical elements comprising a collimating lens arranged to deliver collimated light to the first lens; a pinhole located at a focal point of the collimating lens on a side of the collimating lens away from the first lens, the pinhole comprising a tip of an optical fiber; and a mechanism for scanning the pinhole in at least one dimension transverse to the axial direction;
   the mechanism for scanning the pinhole comprises a second electromagnet spaced apart from a first cantilever beam in the transverse dimension,
   the first cantilever beam projects from a support in the axial direction, and
   the pinhole is mounted to the first cantilever beam, and the first cantilever beam comprises a magnetic material.

2. An optical scanning device according to claim 1 wherein the flexure comprises a plurality of folded beams coupling the mounting portion to a support.

3. An optical scanning device according to claim 2 wherein the folded beams extend between the mounting portion and a frame.

4. An optical scanning device according to claim 3 wherein the mounting portion, folded beams and frame are integrally formed in a sheet of material.

5. An optical scanning device according to claim 4 wherein the material is a ferromagnetic material.

6. An optical scanning device according to claim 5 wherein the material is nickel or a nickel alloy.

7. An optical scanning device according to claim 1 wherein the flexure comprises four folded beams coupled to the mounting portion at points equally spaced apart around a periphery of the mounting portion.

8. An optical scanning device according to claim 7 wherein the mounting portion is square.

9. An optical scanning device according to claim 1 wherein the mounting portion is formed with an aperture and the first lens is mounted in the aperture.

10. An optical scanning device according to claim 9 wherein an optical axis of the first lens is aligned in the axial direction.

11. An optical scanning device according to claim 10 wherein the first lens has a numerical aperture in the range of 0.1 to 0.7.

12. An optical scanning device according to claim 1 wherein the first cantilever beam has a ratio of width to thickness of at least 10:1 and the first cantilever beam is oriented so that a face of the first cantilever beam faces the second electromagnet.

13. An optical scanning device according to claim 12 wherein the first cantilever beam comprises a longitudinal groove and the optical fiber is affixed along the longitudinal groove.

14. An optical scanning device according to claim 12 wherein the first cantilever beam is made of nickel or a nickel alloy.

15. An optical scanning device according to claim 1 wherein the first cantilever beam is supported at an end of a second cantilever beam and the second cantilever beam has a bending axis aligned at right angles with a bending axis of the first cantilever beam.

16. An optical scanning device according to claim 15 comprising an electromagnetic actuator configured to flex the second cantilever beam about its bending axis, the electromagnetic actuator comprising a coil having windings extending around the second cantilever beam and a magnet mounted to the second cantilever beam at a point spaced apart from a fixed end of the second cantilever beam, the magnet having a pole spaced apart from a longitudinal axis of the second cantilever beam.

17. An optical scanning device according to claim 15 wherein the second cantilever beam has a stiffness about its bending axis that greater than a stiffness of the first cantilever beam about a bending axis of the first cantilever beam.

18. An optical scanning device according to claim 17 wherein the stiffness of the second cantilever beam is at least twice as great as the stiffness of the first cantilever beam.

* * * * *